United States Patent [19]

Sprecher et al.

[11] Patent Number: 5,436,153
[45] Date of Patent: Jul. 25, 1995

[54] HUMAN AMYLOID PROTEIN PRECURSOR HOMOLOG AND KUNITZ-TYPE INHIBITOR

[76] Inventors: Cindy A. Sprecher, 8207 - 39th Ave., NE., Seattle, Wash. 98115; Donald C. Foster, 3002 NE. 181st St., Seattle, Wash. 98155; Kjeld E. Norris, Ahlmanns Alle 34, 2900 Hellerup, Denmark

[21] Appl. No.: 985,692

[22] Filed: Dec. 2, 1992

[51] Int. Cl.$^6$ .............. C12N 5/00; C12N 9/48; C12P 21/06; C07H 19/00
[52] U.S. Cl. .............. 435/240.2; 435/6; 435/69.1; 435/212; 435/213; 435/252.3; 435/320.1; 536/22.1; 536/23.1; 536/23.2; 536/23.5
[58] Field of Search .............. 435/6, 69.1, 212, 213, 435/252.3, 320.1, 240.2; 536/22.1, 23.1, 23.2, 23.5

[56] References Cited

FOREIGN PATENT DOCUMENTS 586790 4/1993 European Pat. Off. .
90/14841 12/1990 WIPO .
93/14200 7/1993 WIPO .

OTHER PUBLICATIONS

Bram et al., *Mol. Cell. Biol.* 7:403–409, 1987.
Yan et al., *Proc. Natl. Acad. Sci. USA* 87:2405–2408, 1990.
Von der Kammer et al., *EMBL/Genbank Data Libraries* Z22572, 1993.
Wasco et al., *Nature Genet,* 5:95–99, 1993.
Sprecher et al., *Biochemistry* 32:4481–4486, 1993.
Kido et al., *Biochim. Biophys. Res. Comm.* 167:716–721, 1990.
Holtzman et al., *Trends in Biochem. Sci.* 16:140–144, 1991.
Adams et al., *Nature* 355:632–634, 1992.
Kitaguchi et al., *Nature* 331:530–532, 1988.
Tanzi et al., *Nature* 331:528–530, 1988.
Jacobsen et al., *Neurobiol. of Aging* 12:575–583, 1991.
Johnstone et al., *Biochem. Biophys. Res. Comm.* 163:1248–1255, 1989.
Oltersdorf et al., *Nature* 341:144–147, 1989.
Smith et al., *Science* 248:1126–1128, 1990.
De Sauvage and Octvae, *Science* 245:651–653, 1989.
Kido et al., *Biochem. Biophys. Res. Comm.* 167:716–721, 1990.
Ponte et al., *Nature* 331:525–527, 1988.

*Primary Examiner*—Robert A. Wax
*Assistant Examiner*—Hyosuk Kim
*Attorney, Agent, or Firm*—Deborah Sawislak

[57] ABSTRACT

The present invention provides isolated DNA molecules comprising a DNA segment encoding a novel human amyloid protein precursor homolog and Kunitz-type inhibitor. Also provided are DNA constructs comprising a first DNA segment encoding a novel human amyloid protein precursor homolog or a Kunitz-type inhibitor wherein said first DNA segment is operably linked to additional DNA segments required for the expression for the first DNA segment, as well as host cells containing such DNA constructs and methods for producing proteins from the host cells.

13 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 399 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: ZGKI13 and ZGKI20

( i x ) FEATURE:
        ( A ) NAME/KEY: CDS
        ( B ) LOCATION: 3..398

( x i ) SEQUENCE DESCRIPTION: SEQ ID NO:1:

```
CA  GCT  GTG  GAT  GAG  GAT  GAT  GAG  GAT  GAG  GAA  GAA  GGG  GAG  GAA  GTG        4 7
    Ala  Val  Asp  Glu  Asp  Asp  Glu  Asp  Glu  Glu  Glu  Gly  Glu  Glu  Val
    1                 5                      10                      15

GTG  GAG  GAC  CGA  GAT  TAC  TAC  TAT  GAC  ACC  TTC  AAA  GGA  GAT  GAC  TAC        9 5
Val  Glu  Asp  Arg  Asp  Tyr  Tyr  Tyr  Asp  Thr  Phe  Lys  Gly  Asp  Asp  Tyr
                         20                  25                      30

AAT  GAG  GAG  AAT  CCT  ACT  GAA  CCC  GGC  AGC  GAC  GGC  ACC  ATG  TCA  GAC        143
Asn  Glu  Glu  Asn  Pro  Thr  Glu  Pro  Gly  Ser  Asp  Gly  Thr  Met  Ser  Asp
                 35                      40                  45

AAG  GAA  ATT  ACT  CAT  GAT  GTC  AAA  GCT  GTC  TGC  TCC  CAG  GAG  GCG  ATG        191
Lys  Glu  Ile  Thr  His  Asp  Val  Lys  Ala  Val  Cys  Ser  Gln  Glu  Ala  Met
             50                      55                  60

ACG  GGG  CCC  TGC  CGG  GCC  GTG  ATG  CCT  CGT  TGG  TAC  TTC  GAC  CTC  TCC        239
Thr  Gly  Pro  Cys  Arg  Ala  Val  Met  Pro  Arg  Trp  Tyr  Phe  Asp  Leu  Ser
     65                      70                  75

AAG  GGA  AAG  TGC  GTG  CGC  TTT  ATA  TAT  GGT  GGC  TGC  GGC  GGC  AAC  AGG        287
Lys  Gly  Lys  Cys  Val  Arg  Phe  Ile  Tyr  Gly  Gly  Cys  Gly  Gly  Asn  Arg
80                       85                  90                      95
```

| | | | | | | | | | | | | | | | | |
|---|---|---|---|---|---|---|---|---|---|---|---|---|---|---|---|---|
| AAC | AAT | TTT | GAG | TCT | GAG | GAT | TAT | TGT | ATG | GCT | GTG | TGT | AAA | GCG | ATG | 335 |
| Asn | Asn | Phe | Glu | Ser | Glu | Asp | Tyr | Cys | Met | Ala | Val | Cys | Lys | Ala | Met | |
| | | | | 100 | | | | 105 | | | | | 110 | | | |
| ATT | CCT | CCA | ACT | CCT | CTG | CCA | ACC | AAT | GAT | GTT | GAT | GTG | TAT | TTC | GAG | 383 |
| Ile | Pro | Pro | Thr | Pro | Leu | Pro | Thr | Asn | Asp | Val | Asp | Val | Tyr | Phe | Glu | |
| | | | 115 | | | | 120 | | | | | 125 | | | | |
| ACC | TCT | GCA | GAT | GAT | A | | | | | | | | | | | 399 |
| Thr | Ser | Ala | Asp | Asp | | | | | | | | | | | | |
| | | | 130 | | | | | | | | | | | | | |

( 2 ) INFORMATION FOR SEQ ID NO:2:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Ala | Val | Asp | Glu | Asp | Asp | Glu | Asp | Glu | Glu | Gly | Glu | Glu | Val | Val |
| 1 | | | | 5 | | | | | 10 | | | | | 15 |
| Glu | Asp | Arg | Asp | Tyr | Tyr | Tyr | Asp | Thr | Phe | Lys | Gly | Asp | Asp | Tyr | Asn |
| | | | 20 | | | | | 25 | | | | | 30 | | |
| Glu | Glu | Asn | Pro | Thr | Glu | Pro | Gly | Ser | Asp | Gly | Thr | Met | Ser | Asp | Lys |
| | | | 35 | | | | | 40 | | | | | 45 | | |
| Glu | Ile | Thr | His | Asp | Val | Lys | Ala | Val | Cys | Ser | Gln | Glu | Ala | Met | Thr |
| | | 50 | | | | 55 | | | | | 60 | | | | |
| Gly | Pro | Cys | Arg | Ala | Val | Met | Pro | Arg | Trp | Tyr | Phe | Asp | Leu | Ser | Lys |
| 65 | | | | | 70 | | | | | 75 | | | | | 80 |
| Gly | Lys | Cys | Val | Arg | Phe | Ile | Tyr | Gly | Gly | Cys | Gly | Gly | Asn | Arg | Asn |
| | | | | 85 | | | | | 90 | | | | | 95 | |
| Asn | Phe | Glu | Ser | Glu | Asp | Tyr | Cys | Met | Ala | Val | Cys | Lys | Ala | Met | Ile |
| | | | | 100 | | | | 105 | | | | | 110 | | |
| Pro | Pro | Thr | Pro | Leu | Pro | Thr | Asn | Asp | Val | Asp | Val | Tyr | Phe | Glu | Thr |
| | | | 115 | | | | 120 | | | | | 125 | | | |
| Ser | Ala | Asp | Asp | | | | | | | | | | | | |
| | | | 130 | | | | | | | | | | | | |

( 2 ) INFORMATION FOR SEQ ID NO:3:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 77..235

( x i ) SEQUENCE DESCRIPTION: SEQ ID NO:3:

| | | | | | |
|---|---|---|---|---|---|
| GAATTCCATT | CAAGAATAGT | TCAAACAAGA | AGATTACAAA | CTATCAATTT | CATACACAAT | 60 |

| | | | | | | | | | | | | | | | |
|---|---|---|---|---|---|---|---|---|---|---|---|---|---|---|---|
| ATAAACGACC | AAAAGA | ATG | AAG | GCT | GTT | TTC | TTG | GTT | TTG | TCC | TTG | ATC | | | 109 |
| | | Met | Lys | Ala | Val | Phe | Leu | Val | Leu | Ser | Leu | Ile | | | |
| | | 1 | | | | 5 | | | | | 10 | | | | |
| GGA | TTC | TGC | TGG | GCC | CAA | CCA | GTC | ACT | GGC | GAT | GAA | TCA | TCT | GTT | GAG | 157 |
| Gly | Phe | Cys | Trp | Ala | Gln | Pro | Val | Thr | Gly | Asp | Glu | Ser | Ser | Val | Glu |
| | | | | 15 | | | | | 20 | | | | | 25 | |
| ATT | CCG | GAA | GAG | TCT | CTG | ATC | ATC | GCT | GAA | AAC | ACC | ACT | TTG | GCT | AAC | 205 |
| Ile | Pro | Glu | Glu | Ser | Leu | Ile | Ile | Ala | Glu | Asn | Thr | Thr | Leu | Ala | Asn |
| | | 30 | | | | | 35 | | | | | 40 | | | |
| GTC | GCC | ATG | GCT | GAG | AGA | TTG | GAG | AAG | AGA | | | | | | | 235 |
| Val | Ala | Met | Ala | Glu | Arg | Leu | Glu | Lys | Arg | | | | | | |

( 2 ) INFORMATION FOR SEQ ID NO:4:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
            20                  25                  30

Leu Ile Ile Ala Glu Asn Thr Thr Leu Ala Asn Val Ala Met Ala Glu
        35                  40                  45

Arg Leu Glu Lys Arg
        50
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4792

( x i ) SEQUENCE DESCRIPTION: SEQ ID NO:5:

GTTGTTGCTG TTGCCTCCGC AGCCTCCGTA        30

( 2 ) INFORMATION FOR SEQ ID NO:6:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: M-1251

( x i ) SEQUENCE DESCRIPTION: SEQ ID NO:6:

GCTGAGAGAT TGGAGAAGAG AGCTGTCTGC TCCCAGGAGG C        42

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: M-1252

( x i ) SEQUENCE DESCRIPTION: SEQ ID NO:7:

AGTTGGTCTA GATTACGCTT TACACACAGC CATAC        35

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (v i i) IMMEDIATE SOURCE:
  (B) CLONE: NOR-1478

(x i) SEQUENCE DESCRIPTION: SEQ ID NO:8:

GTAAAACGAC GGCCAGT                                                              17

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (v i i) IMMEDIATE SOURCE:
    (B) CLONE: NOR-2523

(x i) SEQUENCE DESCRIPTION: SEQ ID NO:9:

TCTCTTCTCC AATCTCTCAG C                                                         21

(2) INFORMATION FOR SEQ ID NO:10:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (v i i) IMMEDIATE SOURCE:
    (B) CLONE: M-1249

(x i) SEQUENCE DESCRIPTION: SEQ ID NO:10:

GCTGAGAGAT TGGAGAAGAG AGATGTCAAA GCTGTCTGCT CCC                                 43

(2) INFORMATION FOR SEQ ID NO:11:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (v i i) IMMEDIATE SOURCE:
    (B) CLONE: M-1250

(x i) SEQUENCE DESCRIPTION: SEQ ID NO:11:

GCTGAGAGAT TGGAGAAGAG AGAAGTCTGC TCCCAGGAGG C                                   41

HUMAN AMYLOID PROTEIN PRECURSOR HOMOLOG AND KUNITZ-TYPE INHIBITOR

TECHNICAL FIELD

The present invention related generally to human amyloid protein precursor homologs and Kunitz-type inhibitors, and more specifically to methods of producing large quantities of such proteins through recombinant DNA techniques.

BACKGROUND OF THE INVENTION

Polymorphonuclear leukocytes (neutrophils or PMNs) and mononuclear phagocytes (monocytes) play an important part in tissue injury, infection, acute and chronic inflammation and wound healing. The cells migrate from the blood to the site of inflammation and, following appropriate stimulation, they release oxidant compounds ($O_2$·, $O_2^-$, $H_2O_2$ and HOCl) as well as granules containing a variety of proteolytic enzymes. The secretory granules contain, inter alia, alkaline phosphatase; metalloproteinases such as gelatinase and collagenase; and serine proteases such as neutrophil elastase, cathepsin G and proteinase-3.

Latent metalloproteinases are released together with tissue inhibitor of metalloproteinase (TIMP). The activation mechanism has not been fully elucidated, but it is likely that oxidation of thiol groups and/or proteolysis play a part in the process. Also, free metalloproteinase activity is dependent on inactivation of TIMP.

In the azurophil granules of polymorphonuclear leukocytes, the serine proteases neutrophil elastase, cathepsin G and proteinase-3 are packed as active enzymes complexed with glucosaminoglycans. These complexes are inactive but dissociate on secretion to release the active enzymes. To neutralize the protease activity, large amounts of the inhibitors $\alpha_1$-proteinase inhibitor ($\alpha_1$-PI) and $\alpha_1$-chymotrypsin inhibitor ($\alpha_1$-ChI) are found in plasma. However, the PMNs are able to inactivate the inhibitors locally. Thus, $\alpha_1$-PI, which is the most important inhibitor of neutrophil elastase, is sensitive to oxidation at the reactive center (Met-358) by oxygen metabolites produced by stimulated PMNs. This reduces the affinity of $\alpha_1$-PI for neutrophil elastase by approximately 2000 times.

After local neutralization of $\alpha_1$-PI, the elastase is able to degrade a number of inhibitors of other proteolytic enzymes. Elastase cleaves $\alpha_1$-ChI and thereby promotes cathepsin G activity. It also cleaves TIMP, resulting in tissue degradation by metalloproteinases. Furthermore, elastase cleaves antithrombin III, heparin cofactor II, and tissue factor pathway inhibitor (TFPI), which probably promotes clot formation. On the other hand, the ability of neutrophil elastase to degrade coagulation factors is assumed to have the opposite effect, such that the total effect of elastase is unclear. The effect of neutrophil elastase on fibrinolysis is less ambiguous. Fibrinolytic activity increases when elastase cleaves plasminogen activator inhibitor and $\alpha_2$ plasmin inhibitor. Furthermore, both of these inhibitors are oxidized and inactivated by $O_2$ metabolites.

PMNs contain large quantities of serine proteases, and about 200 mg of each of the leukocyte proteases are released daily to deal with invasive agents in the body. Acute inflammation leads to a many-fold increase in the amount of enzyme released. Under normal conditions, proteolysis is kept at an acceptably low level by large amounts of the inhibitors $\alpha_1$-PI, $\alpha_1$-ChI and $\alpha_2$ macroglobulin present in plasma. There is some indication, however, that a number of chronic diseases are caused by pathological proteolysis due to overstimulation of the PMNs. Such overstimulation may be caused by, for instance, autoimmune response, chronic infection, tobacco smoke or other irritants, etc.

Protein inhibitors are classified into a series of families based on extensive sequence homologies among the family members and the conservation of intrachain disulfide bridges (for review, see Laskowski and Kato, Ann. Rev. Biochem. 49: 593-626, 1980). Serine protease inhibitors of the Kunitz family are characterized by their homology with aprotinin (bovine pancreatic trypsin inhibitor). Aprotinin is known to inhibit various serine proteases including trypsin, chymotrypsin, plasmin and kallikrein. Kunitz-type inhibitor domains have been reported in larger proteins such as the inter-$\alpha$-trypsin inhibitors (Hochstrasser et al., Hoppe-Seylers Z. Physiol. Chem. 357: 1659-1661, 1969 and Tschesche et al., Eur. J. Biochem. 16: 187-198, 1970) and the $\beta$-amyloid protein precursor. The $\beta$-amyloid protein precursor (APP) contains an approximately 40 amino acid fragment that forms the senile plaques observed in Alzheimer's patients, patients with Down's syndrome and in aged normal patients. The gene encoding APP yields three alternatively spliced mRNAs, two of which have been demonstrated to encode Kunitz-type inhibitor domains (see Ponte et al., Nature 331: 525-528, 1988; Tanzi et al., Nature 331: 528-530, 1988 and Kitaguchi et al., Nature 331: 530-532, 1988). In addition to the Kunitz-type inhibitor domain, each protein precursor contains a signal peptide, a cysteine-rich region, a highly negatively charged region, a transmembrane domain and an intracellular domain (see Kitaguchi et al. ibid.).

Of the Kunitz-type inhibitors, aprotinin is used therapeutically in the treatment of acute pancreatitis, various states of shock syndrome, hyperfibrinolytic hemorrhage and myocardial infarction (see, for example, Trapnell et al., Brit. J. Surg. 61: 177, 1974; McMichan et al., Circulatory shock 9: 107, 1982; Auer et al., Acta Neurochir. 49: 207, 1979; Sher, Am. J. Obstet. Gynecol. 129: 164, 1977; and Schneider, Artzneim.-Forsch. 26: 1606, 1976). Administration of aprotinin in high doses significantly reduces blood loss in connection with cardiac surgery, including cardiopulmonary bypass operations (see, for example, Bidstrup et al., J. Thorac. Cardiovasc. Surg. 97: 364-372, 1989; van Oeveren et al., Ann. Thorac. Surg. 44: 640-645, 1987). It has previously been demonstrated (Wenzel and Tschesche, Angew. Chem. Internat. Ed. 20: 295, 1981) that certain aprotinin analogues, e.g. aprotinin (1-58, Val15), exhibit a relatively high selectivity for granulocyte elastase and an inhibitory effect on collagenase. Aprotinin (1-58, Ala15) has a weak effect on elastase, while aprotinin (3-58, Arg15, Ala17, Ser42) exhibits an excellent plasma kallikrein inhibitory effect (WO 89/10374).

However, when administered in vivo, aprotinin has been found to have a nephrotoxic effect in rats, rabbits and dogs after repeated injections of relatively high doses (Bayer, Trasylol, Inhibitor of Proteinase; Glaser et al. in "Verhandlungen der Deutschen Gesellschaft für Innere Medizin, 78. Kongress," Bergmann, Munich, 1972, pp. 1612-1614). The nephrotoxicity (appearing, i.e., in the form of lesions) observed for aprotinin might be ascribed to the accumulation of aprotinin in the proximal tubulus cells of the kidneys as a result of the high positive net charge of aprotinin, which causes it to be bound to the negatively charged surfaces of the tubuli. This nephrotoxicity makes aprotinin less suitable for clinical purposes, particularly in those uses requiring administration of large doses of the inhibitor (such as cardiopulmonary bypass operations). Furthermore, aprotinin is a bovine protein, which may induce an immune response upon administration to humans.

It is therefore an object of the present invention to provide novel human protease inhibitors of the Kunitz family of inhibitors with similar inhibitor profiles for use in the treatment of acute pancreatitis, various states of shock syndrome, hyperfibrinolytic hemorrhage and myocardial infarction. It is further an object of the present invention to provide novel amyloid protein precursor homologs for use in studying the relative levels of the precursor in patients exhibiting Alzheimer's disease and to identify patients with mutations in the protein precursor.

SUMMARY OF THE INVENTION

Briefly stated, the present invention provides novel isolated DNA molecules encoding human amyloid protein precursor homolog and human Kunitz-type inhibitor. Within one embodiment of the invention, the DNA molecule comprises a DNA segment encoding a human amyloid protein precursor homolog, wherein the DNA segment comprises the sequence of nucleotides of Sequence ID No. 1 from nucleotide 1 to nucleotide 399. Within another embodiment, the DNA segment encodes a human amyloid protein precursor homolog comprising the amino acid sequence of Sequence ID No. 2 from alanine, amino acid number 1, to asparagine, amino acid number 132. Also provided are DNA constructs comprising a first DNA segment encoding a human amyloid protein precursor homolog operably linked to additional DNA segments necessary for the expression of the first DNA segment, host cells containing such DNA constructs, as well as methods for producing a human amyloid protein precursor homolog comprising the step of culturing a host cell under conditions promoting the expression of a DNA segment encoding a human amyloid precursor protein homolog.

Within another aspect of the invention, DNA molecules are provided which comprise a DNA segment encoding a human Kunitz-type inhibitor, wherein the DNA segment comprises the sequence of nucleotides of Sequence ID No. 1 from nucleotide 171 to nucleotide 331 or the sequence of nucleotides of Sequence ID No. 1 from nucleotide 159 to nucleotide 331. Within another embodiment, the DNA segment encodes a human Kunitz-type inhibitor comprising the amino acid sequence of Sequence ID No. 2 from alanine, amino acid 56 to alanine, amino acid number 110; the amino acid sequence of Sequence ID No. 2 from aspartic acid, amino acid number 53 to alanine, amino acid number 110; or the amino acid sequence of Sequence ID No. 2 from valine, amino acid number 57 to alanine, amino acid number 110 and which further contains a glutamic acid residue on the amino terminus. Also provided are DNA constructs comprising a first DNA segment encoding a human Kunitz-type inhibitor operably linked to additional DNA segments necessary for the expression of the first DNA segment, host cells containing such DNA constructs, as well as methods for producing a human Kunitz-type inhibitor comprising the step of culturing a host cell under conditions promoting the expression of a DNA segment encoding a human Kunitz-type inhibitor.

Within another aspect of the invention, isolated amyloid precursor proteins and Kunitz-type inhibitors are provided. Within one embodiment, an isolated amyloid protein precursor homolog comprises the amino acid sequence of Sequence ID No. 2 from alanine, amino acid number 1, to Asparagine, amino acid number 132. Within another embodiment, an isolated human Kunitz-type inhibitor comprises the amino acid sequence of Sequence ID No. 2 from alanine, amino acid 56 to alanine, amino acid number 110; the amino acid sequence of Sequence ID No. 2 from aspartic acid, amino acid number 53 to alanine, amino acid number 110; or the amino acid sequence of Sequence ID No. 2 from valine, amino acid number 57 to alanine, amino acid number 110 and which further contains a glutamic acid residue on the amino terminus.

Within another aspect of the invention, isolated antibodies are provided with specifically bind to a human amyloid protein precursor or to a human Kunitz-type inhibitor. Within one embodiment, the antibody is a monoclonal antibody.

Within yet another aspect of the invention, a pharmaceutical composition is provided which comprises a human Kunitz-type inhibitor comprising the amino acid sequence of Sequence ID No. 2 from alanine, amino acid 56 to alanine, amino acid number 110; the amino acid sequence of Sequence ID No. 2 from aspartic acid, amino acid number 53 to alanine, amino acid number 110; or the amino acid sequence of Sequence ID No. 2 from valine, amino acid number 57 to alanine, amino acid number 110 and which further contains a glutamic acid residue on the amino terminus.

Within another aspect of the invention, probes of at least 12 nucleotides are provided, wherein the probes are capable of hybridizing with nucleic acids encoding a human amyloid protein precursor homolog or a Kunitz-type inhibitor domain comprising the nucleotide sequence of Sequence ID No. 1, nucleotide variants of Sequence ID No. 1, or DNA segments encoding DNA sequences complementary to Sequence ID No. 1 or its variants.

These and other aspects will become evident upon reference to the following detailed description.

DETAILED DESCRIPTION OF THE INVENTION

The present invention provides a novel human amyloid protein precursor containing a protease inhibitor domain that shares homology with the Kunitz family of protease inhibitors. The Kunitz-type inhibitor of the present invention has the advantage that it has a negative net charge as opposed to aprotinin, which may thereby reduce the risk of kidney damage on administration of large doses of the inhibitor. Another advantage is that, contrary to aprotinin, the inhibitor of the present invention is a human protein, so that undesired immunological reactions on administration to humans are significantly reduced. The amyloid protein precursor homologs of the present invention and the DNA sequences encoding such proteins provide the advantage of allowing the expression of such proteins in patients with Alzheimer's disease to be compared with the expression of such protein in normal patients.

A feature of the present invention is an isolated DNA molecule encoding a human Kunitz-type inhibitor. Another feature of the present invention is an isolated DNA molecule encoding a human amyloid protein precursor homolog. Such isolated molecules are those that are separated from their natural environment and include cDNA and genomic clones. Isolated DNA molecules of the present invention are provided free of other genes with which they are naturally associated and may include naturally occurring 5' and 3' untranslated sequences that represent regulatory regions such as promoters and terminators. The identification of regulatory regions within the naturally occurring 5' and 3' untranslated regions will be evident to one of ordinary skill in the art (for review, see Dynan and Tijan, *Nature* 316: 774–778, 1985; Birnstiel et al., *Cell* 41: 349–359, 1985; Proudfoot, *Trends in Biochem. Sci.* 14: 105–110, 1989; and Sambrook et al., *Molecular Cloning: A Laboratory Manual, Second Edition*, Cold Spring Harbor, N.Y., 1989; which are incorporated herein by reference).

The isolated DNA molecules of the present invention are useful in producing recombinant human Kunitz-type inhibitors and recombinant human amyloid protein precursor homologs. Thus, the present invention provides the advantage that human Kunitz-type inhibitors and amyloid protein precursor homologs are produced in high quantities that may be readily purified using methods known in the art (see generally, Scopes, Protein Purification, Springer-Verlag, N.Y., 1982). Alternatively, the proteins of the present invention may be synthesized following any suitable method, such as by exclusively solid-phase techniques, by partial solid-phase techniques, by fragment condensation or by classical solution addition. Synthetic polypeptides of the present invention may be prepared by manual synthesis or using a suitable peptide synthesizer.

Kunitz-type inhibitor activity may be measured using the method essentially described by Norris et al. (*Biol. Chem. Hoppe-Seyler* 371: 37–42, 1990). Briefly, various fixed concentrations of the Kunitz-type inhibitor are incubated in the presence of 0.24 µg/ml of porcine trypsin (Novo Nordisk A/S, Bagsvaerd, Denmark), 12.8 CU/1 human plasmin (Kabi, Stockholm, Sweden) or 0.16 nkat/ml human plasma kallikrein (Kabi) in 100 mM NaCl, 50 mM Tris HCl, pH 7.4. After a 30 minute incubation, the residual enzymatic activity is measured by the degradation of a solution containing 0.6 mM of either of the chromogenic peptidyl nitroanilide trypsin/plasmin substrates S2251 (D-Val-Leu-Lys-Nan; Kabi) or S2302 (D-Pro-Phe-Arg-Nan; Kabi) in assay buffer. The samples are incubated for 30 minutes after which the absorbance of each sample is measured at 405 nm. An inhibition of plasmin or trypsin activity is measured as a decrease in absorbance at 405 nm. From the results, the apparent inhibition constant Ki is calculated.

The Kunitz-type inhibitors of the present invention may be used in the disclosed methods for the treatment of, inter alia, acute pancreatitis, various states of shock syndrome, hyperfibrinolytic hemorrhage and myocardial infarction. The amyloid protein precursor homologs of the present invention may be used, inter alia, to generate antibodies for use in demonstrating tissue distribution of the precursor or for use in purifying such proteins.

Thus, an additional feature of the present invention is an isolated human Kunitz-type inhibitor or an isolated human amyloid protein precursor homolog. Isolated proteins and peptides of the present invention are proteins of at least about 50% homogeneity, more preferably of 70% to 80% homogeneity with a protein preparation of 95% to 99% or more homogeneity most preferred, particularly for pharmaceutical uses.

The present invention relates to a novel human amyloid protein precursor homolog containing a human Kunitz-type inhibitor comprising the amino acid sequence shown in Sequence ID Nos. 1 and 2 and/or encoded by a DNA sequence comprising the nucleotide sequence of Sequence ID No. 1. The Kunitz-type inhibitors of the present invention are up to 80 amino acids, preferably between 50 and 60 amino acids, most preferably between 53 and 57 amino acids in length and comprise the amino acid sequence shown Sequence I.D. Nos. 1 and 2 from valine, amino acid number 57 through alanine, amino acid number 110. However, as will be evident to skilled in the art, amino-terminal and/or carboxy-terminal extensions of the Kunitz-type inhibitor may be prepared either synthetically or using recombinant DNA techniques and tested for inhibitor activity.

The DNA sequences encoding the proteins of the present invention were unexpectedly identified during screening for a cDNA corresponding to the genomic clone of an unrelated Kunitz-type inhibitor using an antisense oligonucleotide probe corresponding to a portion of the inhibitor coding sequence. Analysis of the cDNA clones revealed that the clones encoded a unique, previously unknown amyloid protein precursor homolog containing a Kunitz-type inhibitor domain. As used herein, the proteins of the present invention may be encoded by DNA sequences that are substantially similar to the DNA sequence disclosed herein. As used within the context of the present invention, "substantially similar" DNA sequences encompasses allelic variants and genetically engineered or synthetic variants of the amyloid protein precursor homolog gene or Kunitz-type inhibitor domain of the amyloid protein precursor homolog gene that contain conservative amino acid substitutions and/or minor additions, substitutions or deletions of amino acids. DNA sequence variants also encompass degeneracies in the DNA code wherein host-preferred codons are substituted for the analogous codons in the human sequence. In addition, substantially similar DNA sequences are those that are capable of hybridizing to the DNA sequences of the present invention under high or low stringency (see Sambrook et al., ibid.) and those sequences that are degenerate as a result of the genetic code to the amino acid sequences of the present invention. Genetically engineered variants may be obtained by using oligonucleotide-directed site-specific mutagenesis, by use of restriction endonuclease digestion and adapter ligation, or other methods well established in the literature (see for example, Sambrook et al., ibid. and Smith et al., *Genetic Engineering: Principles and Methods*, Plenum Press, 1981; which are incorporated herein by reference).

DNA sequences of the present invention may be isolated using standard cloning methods such as those described by Maniatis et al. (*Molecular Cloning: A Laboratory Manual*, Cold Spring Harbor, N.Y., 1982; which is incorporated herein by reference), Sambrook et al. (*Molecular Cloning: A Laboratory Manual, Second Edition*, Cold Spring Harbor, N.Y., 1989; which is incorporated herein by reference) or Mullis et al. (U.S. Pat. No. 4,683,195; incorporated herein by reference). Alternatively, the coding sequences of the present invention may be synthesized using standard techniques that are well known in the art, such as by synthesis on an automated DNA synthesizer. As will be discussed in more detail below, a novel human amyloid protein precursor homolog containing a Kunitz-type inhibitor domain was identified as a 3.5 kb cDNA insert and comprises the DNA sequence of Sequence I.D. No. 1. In a preferred embodiment, DNA sequences encoding Kunitz-type inhibitors are obtained by PCR amplification using primers designed from Sequence ID No. 1 or its complement.

DNA molecules of the present invention or portions thereof may be used, for example, to directly detect amyloid protein precursor homolog sequences in cells. Such DNA molecules are generally synthetic oligonucleotides, but may be generated from cloned cDNA or genomic sequences and will generally comprise more than 12 nucleotides, more often from about 14 nucleotides to about 25 or more nucleotides, sometimes 40 to 60 nucleotides, and in some instances a substantial portion or even the entire cDNA of the amyloid protein precursor homolog gene. The synthetic oligonucleotides of the present invention are at least 85% homologous to a corresponding DNA sequence of the human amyloid protein precursor homolog of Sequence ID Number 1 or its complement. For use as probes, the molecules are labeled to provide a detectable signal, such as with an enzyme, biotin, a radionuclide, fluorophore, chemiluminescer, paramagnetic particle, etc. according to methods known in the art.

DNA molecules used within the present invention may be labeled and used in a hybridization procedure similar to the Southern or dot blot. As will be understood by those skilled in the art, conditions that allow the DNA molecules of the present invention to hybridize to amyloid protein precursor homolog sequences or amyloid protein precursor homolog-like sequences may be determined by methods well known in the art and are reviewed, for example, by Sambrook et al. (*Molecular Cloning: A Laboratory Manual, Second Edition,* Cold Spring Harbor, N.Y., 1989; which is incorporated herein by reference). Those skilled in the art will be capable of varying hybridization conditions (i.e. stringency of hybridization) of the DNA molecules as appropriate for use in the various procedures by methods well known in the literature (see, for example, Sambrook et al., ibid., pages 11.45-11.53). The higher the stringency of hybridization, the lower the number of mismatched sequences are detected. Alternatively, lower stringency will allow related sequences to be identified.

Alternatively, human amyloid protein precursor homolog sequence variants may be identified using DNA molecules of the present invention and, for example, the polymerase chain reaction (PCR) (disclosed by Saiki et al., *Science* 239: 487, 1987; Mullis et al., U.S. Pat. No. 4,686,195; and Mullis et al., U.S. Pat. No. 4,683,202) to amplify DNA sequences, which are subsequently detected by their characteristic size on agarose gels or which may be sequenced to detect sequence abnormalities.

Amyloid protein precursor homolog and Kunitz-type inhibitor sequences of the present invention may be inserted into DNA constructs. As used within the context of the present invention, a DNA construct, also known as an expression vector, is understood to refer to a DNA molecule, or a clone of such a molecule, either single- or double-stranded, which has been modified through human intervention to contain segments of DNA combined and juxtaposed in a manner that would not otherwise exist in nature. DNA constructs of the present invention comprise a first DNA segment encoding an amyloid protein precursor homolog or a Kunitz-type inhibitor operably linked to additional DNA segments required for the expression of the first DNA segment. Within the context of the present invention, additional DNA segments will generally include promoters and transcription terminators, and may further include enhancers and other elements. One or more selectable markers may also be included.

In a preferred embodiment the DNA sequence encodes a Kunitz-type inhibitor comprising the amino acid sequence of Sequence ID No. 2 from alanine, amino acid number 56 through alanine, amino acid number 110. In another embodiment, the first DNA sequence encodes a Kunitz-type inhibitor comprising the amino acid sequence of Sequence ID No. 2 from aspartic acid, amino acid 53 to alanine, amino acid 110. In yet another embodiment, the first DNA sequence encodes a Kunitz-type inhibitor comprising the amino acid sequence of Sequence ID No. 2 from valine, amino acid number 57 through alanine, amino acid number 110 and which further contains a codon for glutamic acid immediately upstream of the codon for valine, amino acid number 57.

DNA constructs may also contain DNA segments necessary to direct the secretion of a polypeptide or protein of interest. Such DNA segments may include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptides from the mature proteins as it passes through the secretory pathway. A preferred processing site is a dibasic cleavage site, such as that recognized by the *Saccharomyces cerevisiae* KEX2 gene. A particularly preferred processing site is a Lys-Arg processing site. Processing sites may be encoded within the secretory peptide or may be added to the peptide by, for example, in vitro mutagenesis.

Preferred secretory signals include the α factor signal sequence (prepro sequence: Kurjan and Herskowitz, *Cell* 30.: 933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), and the SUC2 signal sequence (Carlsen et al., *Molecular and Cellular Biology* 3: 439–447, 1983). Alternately, a secretory signal sequence may be synthesized according to the rules established, for example, by von Heinje (*European Journal of Biochemistry* 133: 17–21, 1983; *Journal of Molecular Biology* 184: 99–105, 1985; *Nucleic Acids Research* 14: 4683–4690, 1986). A particularly preferred signal sequence is the synthetic signal LaC212 spx (1-47)—ERLE described in WO 90/10075, which is incorporated by reference herein in its entirety.

Secretory signal sequences may be used singly or may be combined. For example, a first secretory signal sequence may be used in combination with a sequence encoding the third domain of barrier (described in U.S. Pat. No. 5,037,243, which is incorporated by reference herein in its entirety). The third domain of barrier may be positioned in proper reading frame 3' of the DNA segment of interest or 5' to the DNA segment and in proper reading frame with both the secretory signal sequence and a DNA segment of interest.

The choice of suitable promoters, terminators and secretory signals is well within the level of ordinary skill in the art. Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). Proteins of the present invention can also be expressed in filamentous fungi, for example, strains of the fungi Aspergillus (McKnight et al., U.S. Pat. No. 4,935,349, which is incorporated herein by reference). Expression of cloned genes in cultured mammalian cells and in *E. coli*, for example, is discussed in detail in Sambrook et al. (*Molecular Cloning: A Laboratory Manual, Second Edition*, Cold Spring Harbor, N.Y., 1989; which is incorporated herein by reference). As would be evident to one skilled in the art, one could express the proteins of the instant invention in other host cells such as avian, insect and plant cells using regulatory sequences, vectors and methods well established in the literature.

In yeast, suitable yeast vectors for use in the present invention include YRp7 (Struhl et al., *Proc. Natl. Acad. Sci. USA* 76: 1035-1039, 1978), YEp13 (Broach et al., *Gene* 8: 121-133, 1979), POT vectors (Kawasaki et al, U.S. Pat. No. 4,931,373, which is incorporated by reference herein), pJDB249 and pJDB219 (Beggs, *Nature* 275:104-108, 1978) and derivatives thereof. Preferred promoters for use in yeast include promoters from yeast glycolytic genes (Hitzeman et al., *J. Biol. Chem.* 255: 12073-12080, 1980; Alber and Kawasaki, *J. Mol. Appl. Genet.* 1: 419-434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, N.Y., 1982; Ammerer, *Meth. Enzymol.* 101: 192-201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652-654, 1983; Irani and Kilgore, U.S. patent application Ser. No. 07/784,653, CA 1,304,020 and EP 284 044, which are incorporated herein by reference). The expression units may also include a transcriptional terminator. A preferred transcriptional terminator is the TPI1 terminator (Alber and Kawasaki, ibid.).

Host cells containing DNA constructs of the present invention are then cultured to produce amyloid protein precursor homologs or Kunitz-type inhibitors. The cells are cultured according to standard methods in a culture medium containing nutrients required for growth of the particular host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by a selectable marker on the DNA construct or co-transfected with the DNA construct.

Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M, preferably at 0.5M or 1.0M. Cultured mammalian cells are generally cultured in commercially available serum-containing or serum-free media. Selection of a medium appropriate for the particular host cell used is within the level of ordinary skill in the art.

The recombinant amyloid protein precursor homologs or Kunitz-type inhibitors expressed using the methods described herein are isolated and purified by conventional procedures, including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like. Methods of protein purification are known in the art (see generally, Scopes, R., *Protein Purification*, Springer-Verlag, N.Y. (1982), which is incorporated herein by reference) and may be applied to the purification of the recombinant proteins of the present invention.

Preferably, the Kunitz-type inhibitors of the present invention are purified using the method essentially described by Norris et al. (*Biol. Chem. Hoppe-Seyler* 371: 37-42, 1990, which is incorporated by reference herein in its entirety). Briefly, selected transformants are grown in 10 liters of YEPD for approximately 40 hours at 30° C. until an $OD_{600}$ of approximately 25 has been reached. The culture is centrifuged, and the supernatant is decanted. A 300 ml-1000 ml aliquot of supernatant is adjusted to pH 2.3 and applied to a column holding 8 ml of S-Sepharaose (Pharmacia-LKB Biotechnology AS, Alleroed, Denmark) or the like that has been previously equilibrated with 20 mM Bicine, pH 8.7 (Sigma Chemical Co., St. Louis, Mo.). After the column has been extensively washed with 20 mM Bicine, pH 8.7, the Kunitz-type inhibitor is eluted with 30 ml of 20 mM Bicine, pH 8.7 containing 1M NaCl. The eluted material is desalted by application to a Sephadex G-25 column (Pharmacia-LKB Biotechnology AS, Alleroed, Denmark; 2.5×30 cm) or the like that has been equilibrated with 20 mM $NH_4HCO_3$, pH 7.8. The Kunitz-type inhibitor is eluted with 20 mM $NH_4HCO_3$, pH 7.8.

The Kunitz-type inhibitor is further purified and concentrated by chromatography on a Mono S column (Pharmacia-LKB Biotechnology AS, Alleroed, Denmark; 0.5×5 cm) or the like equilibrated with 20 mM Bicine, pH 8.7. After washing with the equilibration buffer at 2 ml/min for 10 minutes, gradient elution of the Kunitz-type inhibitor is carried out over twelve minutes at 1 ml/min from 0–0.6M NaCl in the equilibration buffer. Peak samples are pooled, and the Kunitz-type inhibitor is purified using reverse phase HPLC on a Vydac 214TP510 column (Mikro-lab, Aarhus, Denmark; 1.0×25 cm) or the like with a gradient elution at 4 ml/min from 5% A (0.1% trifluoroacetic acid (TFA) in water) to 45% B (0.7% TFA in acetonitrile) in 20 minutes. The purified product in lyophilized in water, and inhibitor activity is measured.

The present invention also relates to a pharmaceutical composition comprising a Kunitz-type inhibitor of the present invention together with a pharmaceutically acceptable carrier or excipient. In the composition of the invention, the variant may be formulated by any of the established methods of formulating pharmaceutical compositions, e.g. as described in *Remington's Pharmaceutical Sciences*, 1985. The composition may typically be in a form suited for systemic injection or infusion and may, as such, be formulated with sterile water or an isotonic saline or glucose solution.

Kunitz-type inhibitors of the present invention are therefore contemplated to be advantageous to use for the therapeutic applications suggested for native aprotinin or aprotinin analogues with other inhibitor profiles, in particular those which necessitate the use of large aprotinin doses. Therapeutic applications for which the use of the variant of the invention is indicated as a result of its ability to inhibit human serine proteases, e.g. trypsin, plasmin, kallikrein, elastase, cathepsin G and proteinase-3, include (but are not limited to) acute pancreatitis, inflammation, thrombocytopenia, preservation of platelet function, organ preservation, wound healing, shock (including shock lung) and conditions involving hyperfibrinolytic hemorrhage, emphysema, rheumatoid arthritis, adult respiratory distress syndrome, chronic inflammatory bowel disease and psoriasis, in other words diseases presumed to be caused by pathological proteolysis by elastase, cathepsin G and proteinase-3 released from triggered PMNs.

Furthermore, the present invention relates to the use of the Kunitz-type inhibitors as described above for the preparation of a medicament for the prevention or therapy of diseases or conditions associated with pathological proteolysis by proteases released from overstimulated PMNs. As indicated above, it may be an advantage to administer heparin concurrently with the Kunitz-type inhibitors of the present invention.

Apart from the pharmaceutical use indicated above, the Kunitz-type inhibitors as specified above may be used to isolate useful natural substances, e.g. proteases or receptors from human material, which bind directly or indirectly to the Kunitz-type inhibitor, for instance by screening assays or by affinity chromatography.

Within one aspect of the present invention, amyloid protein precursor homologs and Kunitz-type inhibitors, including derivatives thereof, as well as portions or fragments of these proteins, are utilized to prepare antibodies which specifically bind to the amyloid protein precursor homologs and Kunitz-type inhibitors. As used herein, the term "antibodies" includes polyclonal antibodies, monoclonal antibodies, antigen-binding fragments thereof such as F(ab')$_2$ and Fab fragments, as well as recombinantly produced binding partners. These binding partners incorporate the variable regions from a gene which encodes a specifically binding monoclonal antibody. Antibodies are defined to be specifically binding if they bind to the amyloid protein precursor homolog or Kunitz-type inhibitor with a $K_a$ of greater than or equal to $10^7$/M. The affinity of a monoclonal antibody or binding partner may be readily determined by one of ordinary skill in the art (see, Scatchard, *Ann. NY Acad. Sci.* 51: 660–672, 1949).

Methods for preparing polyclonal and monoclonal antibodies have been well described in the literature (see for example, Sambrook et al., ibid.; Hurrell, J. G. R., Ed., *Monoclonal Hybridoma Antibodies: Techniques and Applications*, CRE Press, Inc., Boca Raton, Fla., 1982). As would be evident to one of ordinary skill in the art, polyclonal antibodies may be generated from a variety of warm-blooded animals such as horses, cows, goats, sheep, dogs, chickens, rabbits, mice, or rats. The immunogenicity of an amyloid protein precursor homolog or Kunitz-type inhibitor may be increased through the use of an adjuvant such Freund's complete or incomplete adjuvant. A variety of assays known to those skilled in the art may be utilized to detect antibodies which specifically bind to an amyloid protein precursor homolog or Kunitz-type inhibitor. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immuno-sorbent assays, dot blot assays, inhibition or competition assays, and sandwich assays.

Additional techniques for the preparation of monoclonal antibodies may utilized to construct and express recombinant monoclonal antibodies. Briefly, mRNA is isolated from a B cell population and utilized to create heavy and light chain immunoglobulin cDNA expression libraries in a suitable vector such as the λIMMUNOZAP(H) and λIMMUNOZAP(L) vectors, which may be obtained from Stratocyte (La Jolla, Calif.). These vectors are then screened individually or are co-expressed to form Fab fragments or antibodies (Huse et al., *Science* 246: 1275–1281, 1989; Sastry et al., *Proc. Natl. Acad. Sci. USA* 86: 5728–5732, 1989). Positive plaques are subsequently converted to a non-lytic plasmid which allows high level expression of monoclonal antibody fragments in *E. coli*.

Binding partners such as those described above may also be constructed utilizing recombinant DNA techniques to incorporate the variable regions of a gene which encodes a specifically binding antibody. The construction of these proteins may be readily accomplished by one of ordinary skill in the art (see for example, Larrick et al., *Biotechnology* 7: 934–938, 1989; Reichmann et al., *Nature* 322: 323–327, 1988 and Roberts et al. *Nature* 328: 731–734, 1987). Once suitable antibodies or binding partners have been obtained, they may be isolated or purified by many techniques well described in the literature (see for example, *Antibodies: A Laboratory Manual*, ibid.). Suitable techniques include protein or peptide affinity columns, HPLC or RP-HPLC, purification on protein A or protein G columns or any combination of these techniques. Within the context of the present invention, the term "isolated" as used to define antibodies or binding partners means "substantially free of other blood components."

Antibodies and binding partners of the present invention may be used in a variety of ways. The tissue distribution of amyloid protein precursor homologs, for example, may be determined by incubating tissue slices with a labeled monoclonal antibody which specifically binds to the amyloid protein precursor homolog, followed by detection of the presence of the bound antibody. Labels suitable for use within the present invention are well known in the art and include, among others, fluorescein, isothiocyanate, phycoerythrin, horseradish peroxidase, and colloidal gold. The antibodies of the present invention may also be used for the purification of amyloid protein precursor homologs and Kunitz-type inhibitors of the present invention. The coupling of antibodies to solid supports and their use in purification of proteins is well known in the literature (see for example, *Methods in Molecular Biology, Vol. 1,* Walker (Ed.), Humana Press, New Jersey, 1984, which is incorporated by reference herein in its entirety).

The following examples are offered by way of illustration, not by way of limitation.

EXAMPLE 1

Cloning of An Amyloid Precursor Protein cDNA

Poly(A)+ RNAs from a variety of human tissue sources were screened using an antisense 30-mer oligonucleotide (ZC4792; Sequence ID No. 5). A blot of human poly(A)+ RNA from heart, brain, placenta, liver, lung, skeletal muscle, kidney and pancreas (HUMAN MTN BLOT) was obtained from Clontech Laboratories, Inc. (Palo Alto, Calif.). The blot was prehybridized in a prehybridization solution containing 5X SSPE (Sambrook et al. (*Molecular Cloning: A Laboratory Manual, Second Edition,* Cold Spring Harbor, N.Y., 1989; which is incorporated herein by reference), 2X Denhardt's (Sambrook et al. (*Molecular Cloning: A Laboratory Manual, Second Edition,* Cold Spring Harbor, N.Y., 1989; which is incorporated herein by reference), 0.5% SDS, and 100 µg/ml sonicated salmon sperm DNA for four hours at 55° C. After prehybridization, the prehybridization solution was removed and replaced with prehybridization solution containing $4.7 \times 10^5$ cpm/ml of $^{32}$P-labeled ZC4792 (Sequence ID No. 5). After an overnight incubation at 55° C. the hybridization solution was removed, and the blot was washed once in 2X SSC, 0.05% SDS at room temperature for 20 minutes followed by a wash in 2X SSC, 0.1% SDS for 20 minutes at 55° C. The blot was exposed to film for two and a half hours. The resulting autoradiograph showed a number of bands in most of the lanes, indicating the presence of related sequences in most of the tissues represented in the blot. The blot was washed at a higher stringency in 2X SSC at 60°-65° C. for 30 minutes, and the blot was exposed to film overnight. The second autoradiograph showed the presence of a 1.6 kb band for placenta and liver and an apparently smaller band of approximately 1.2 kb in the pancreas.

To obtain a cDNA sequence encoding a protease inhibitor from the Kunitz family from human placenta, a human placenta cDNA library in λgt11 was screened using the radio-labeled ZC4792 (Sequence ID No. 5). Poly(A)+ RNA was prepared from human placenta and was used to prepare a λgt11 cDNA library essentially as described by Hagen et al. (*Proc. Natl. Acad. Sci. USA* 83: 2412–2416, 1986 and U.S. Pat. No. 4,784,950, which are incorporated herein by reference). The library was titered and 50,000 pfu/plate were plated on a total of twenty plates to obtain one million independent plaques. Duplicate plaque lifts were prepared using ICN BIOTRANS nylon membranes (ICN, Irvine, Calif.). The membranes were prewashed in 5x SSC, 0.5% SDS at 50° C. for one hour followed by an overnight prehybridization at 55° C. in prehybridization solution (5x SSPE, 5x Denhardt's, 0.5% SDS, 100 µg/ml sheared salmon sperm DNA). The prehybridization solution was removed and replaced with prehybridization solution containing $1.6 \times 10^8$ cpm of ZC4792 probe (Sequence ID No. 5). Hybridization was carried out under the same conditions as the prehybridization. The hybridization solution was removed, and the blots were washed at 60° C. in 2x SSC, 0.1% SDS. Eleven positive plaques were identified and plaque purified.

Phage DNA prepared from each purified plaque was digested with Eco RI to isolate the cDNA insert. The Eco RI fragments, which ranged in size from 2.0–3.5 kb, were then subcloned into Eco RI-linearized pUC19. Sequence analysis of the cloned fragments demonstrated that the clones showed some homology to the Kunitz family of protease inhibitors. Selected clones were subjected to extensive sequence analysis and were shown to have strong homology to human amyloid protein precursor homolog (Ponte et al., ibid.), which contains a Kunitz-type inhibitor domain. Two clones, ZGKI13 and ZGKI20, which encoded approximately 3.5 and approximately 2.5 kb cDNA inserts, respectively, were selected for further analysis. Plasmids ZGKI13 and ZGKI20 were deposited on Oct. 14, 1992 with the American Type Culture Collection (12301 Parklawn Dr., Rockville, Md.) under accession numbers 69090 and 69089, respectively. Plasmids ZGKI13 and ZGKI20 were shown to contain the identical sequence shown in Sequence ID Nos. 1 and 2.

EXAMPLE 2

Expression of a Kunitz-Type Inhibitor Domain

The Kunitz-type inhibitor domain encoded in plasmid ZGKI20 and comprising the amino acid sequence of Sequence ID Number 2 from alanine, amino acid 56 through alanine, amino acid number 110 was expressed in a strain of the yeast *Saccharomyces cerevisiae* from a PCR-generated sequence. The DNA sequence encoding the Kunitz-type inhibitor was amplified from human genomic DNA obtained from Clontech (Palo Alto, Calif.). Synthetic oligonucleotide primers M-1252 and M-1251 (Sequence ID Nos. 7 and 6, respectively) were designed as PCR amplification primers. Synthetic oligonucleotide M-1252 is complementary to nucleotides 313–332 of Sequence ID No. 1, and in addition carries a 5' extension containing a translation stop codon followed by an Xba I site. Oligonucleotide M-1251 contains a sequence that is identical to nucleotides 215–235 of the synthetic leader sequence shown in Sequence ID No. 3 followed by nucleotides 168–187 of Sequence ID No. 1. A PCR reaction was performed in a 100 µl final volume using 1 µg of human genomic DNA (Clontech), 100 pmole each of oligonucleotides M-1251 and M-1252 (Sequence ID Nos. 6 and 7, respectively), and the reagents in the GENEAMP kit (Perkin Elmer Cetus, Norwalk, Conn.) according to the manufacturer's instructions. The reaction was amplified for nineteen cycles (20 seconds at 94° C., 20 seconds at 50° C., and 30 seconds at 72° C.) followed by a ten minute incubation at 72° C. A 201 bp fragment was isolated by agarose gel electrophoresis.

A DNA sequence encoding the synthetic signal sequence (Sequence ID No. 3) was obtained by PCR amplification of a fragment from plasmid pKFN-1000. Plasmid pKFN-1000 is a derivative of plasmid pTZ19R (Mead et al., *Prot. Engin.* 1: 67–74, 1986) containing a DNA sequence encoding a synthetic yeast signal leader peptide. Plasmid pKFN-1000 is described in WO 90/10075, which is incorporated by reference herein in its entirety. The DNA sequence of the 235 base pairs downstream from the Eco RI site of plasmid pKFN-1000 and the encoded amino acid sequence is shown in Sequence ID Nos. 3 and 4. A 0.7 kb Pvu II fragment of plasmid pKFN-1000 was used as a template. Synthetic oligonucleotide NOR-1478 (Sequence ID No. 8) is identical to a sequence just upstream of the Eco RI site (nucleotides to 1–6 of Sequence ID No. 3). Synthetic oligonucleotide NOR-2523 (Sequence ID No. 9) is complementary to nucleotides 215–235 of the coding sequence in Sequence ID No. 3. A PCR reaction was performed in a 100 μl final volume using 0.1 μg of the 0.7 kb Pvu II fragment, 100 pmoles each of oligonucleotide NOR-1478 and NOR-2523 (Sequence ID Nos. 8 and 9, respectively) and reagents from the GENEAMP commercial kit (Perkin Elmer Cetus) according to the manufacturer's instructions. The PCR reaction was amplified as described above. A 257 bp PCR product was isolated by agarose gel electrophoresis.

A DNA sequence encoding the complete synthetic signal sequence operatively linked to the Kunitz-type inhibitor sequence was obtained by amplifying the two PCR fragments described above. A PCR reaction was performed as described above using 100 pmoles each of primers NOR-1478 (Sequence ID No. 8) and M-1252 (Sequence ID No. 7) and 0.1 μg of each of the two PCR fragments described above. The PCR reaction was amplified for sixteen cycles (1 minute at 94° C., 2 minutes at 50° C., 3 minutes at 71° C.) followed by a ten minute incubation at 72° C. A 437 bp fragment was purified by agarose gel electrophoresis. The fragment was then digested with Eco RI and Xba I, and the resulting 404 bp fragment was ligated with plasmid pTZ19R, which had been linearized by digestion with Eco RI and Xba I. The ligation mixture was transformed into competent restriction minus, modification plus *E. coli* strain, and transformants were selected in the presence of ampicillin. Plasmid DNAs prepared from selected transformants were sequenced, and a plasmid containing the DNA sequence of the Kunitz-type inhibitor fused to the synthetic yeast signal sequence was identified.

The Eco RI-Xba I fragment encoding the secretory signal-Kunitz-type inhibitor was then isolated and subcloned into Eco RI-Xba I linearized plasmid pMT-636. Plasmid pMT-636 is derived from the shuttle vector pCPOT (Plasmid pCPOT was deposited on May 9, 1984 with the American Type Culture Collection; 12301 Parklawn Dr., Rockville, Md.; under Accession No. 39685) in which the 0.4 kb Hpa I-Nru I fragment containing the *Saccharomyces cerevisiae* LEU2 gene was deleted and, in addition, contains the *Saccharomyces cerevisiae* TPI1 promoter and the TPI1 terminator flanking an Eco RI-Xba I directional cloning site such that the a DNA insert is transcribed in the same direction as the *Schizosaccharomyces pombe* POT1 gene (Norris et al., ibid.) and has been described in WO 89/01968 and WO 90/10075, which are incorporated herein by reference in their entirety.

A plasmid containing the signal sequence-Kunitz-type inhibitor fragment in the correct orientation was transformed into *S. cerevisiae* MT-663 (a/α Δtpi/Δtpi pep4-3/pep4-3). Transformants were selected for growth on glucose as the sole carbon source, and cultivated in YEPD media. Transformants were assayed for activity as described in Example 5. The Kunitz-type inhibitor is purified as described in Example 6.

EXAMPLE 3

Expression of a Kunitz-Type Inhibitor Domain

A DNA construct encoding a Kunitz-type inhibitor comprising the amino acid sequence of Sequence ID Number 2 from aspartic acid, amino acid number 53, through alanine, amino acid number 110, was amplified from human genomic DNA as described in Example 1 using oligonucleotide primers M-1252 and M-1249 (Sequence ID Nos. 7 and 10). The resulting PCR-generated fragment was gel-purified and joined to the signal sequence as described above. The fragment encoding the signal sequence-Kunitz-type inhibitor was then subcloned into a yeast expression vector and transformed into *Saccharomyces cerevisiae* strain MT-663 as described in Example 2.

Selected transformants were assayed for activity as described in Example 5. The Kunitz-type inhibitor is purified as described in Example 6.

EXAMPLE 4

Expression of a Kunitz-Type Inhibitor Domain

A DNA construct encoding a Kunitz-type inhibitor comprising the amino acid sequence of Sequence ID Number 2 from valine, amino acid number 57, through alanine, amino acid number 110, and which further contains a glutamic acid immediately N-terminal to valine was amplified from human genomic DNA as described in Example 1 using oligonucleotide primers M-1252 and M-1250 (Sequence ID Nos. 7 and 11). The resulting PCR-generated fragment was gel-purified and joined to the signal sequence as described above. The fragment encoding the signal sequence-Kunitz-type inhibitor was then subcloned into a yeast expression vector and transformed into *Saccharomyces cerevisiae* strain MT-663 as described in Example 2.

Selected transformants were assayed for activity as described in Example 5. The Kunitz-type inhibitor is purified as described in Example 6.

EXAMPLE 5

Activity Assay on Culture Supernatants

Trypsin inhibitory activity was measured on the spent media from cultures of yeast transformants described in Examples 2, 3 and 4 by diluting 3.2 μl of each spent medium sample with 80 μl of assay buffer (50 mM Tris HCl, pH 7.4, 100 mM NaCl, 2 mM CaCl$_2$, 0.1% w/v PEG 20,000). The diluted supernatant was added to 80 μl of 133 nM bovine trypsin (Novo Nordisk A/S) diluted in assay buffer, and the mixture was incubated for 10 minutes at room temperature. After incubation, 100 μl of 1.8 mM peptidyl nitroanilide substrate S2251 (D-Val-Leu-Lys-Nan; Kabi) diluted in assay buffer was added to each sample, and the samples were incubated with the substrate for 30 minutes. Trypsin inhibitory activity, as indicated by a colorless solution, was found in supernatants from the yeast strains described in Examples 2, 3 and 4. A control reaction, which resulted in a yellow solution, was produced by a supernatant from a yeast strain not expressing any Kunitz-type inhibitor.

EXAMPLE 6

Purification of Kunitz-Type Inhibitors

Kunitz-type inhibitors are purified essentially as described by Norris et al. (ibid.; which is incorporated herein by reference). Selected transformants are grown in 10 liters of YEPD for approximately 40 hours at 30° C. until an OD$_{600}$ of approximately 25 has been reached. The culture is centrifuged, and the supernatant is decanted.

For purification, a 300 ml–1000 ml aliquot of supernatant is adjusted to pH 2.3 and applied to a column holding 8 ml of S-Sepharaose (Pharmacia-LKB Biotechnology AS, Alleroed, Denmark) that has been previously equilibrated with 20 mM Bicine, pH 8.7 (Sigma Chemical Co., St. Louis, Mo.). After the column has been extensively washed with 20 mM Bicine, pH 8.7, the Kunitz-type inhibitor is eluted with 30 ml of 20 mM Bicine, pH 8.7 containing 1M NaCl. The eluted material is desalted by application to a Sephadex G-25 column (Pharmacia-LKB Biotechnology AS, Alleroed, Denmark; 2.5×30 cm) that has been equilibrated with 20 mM NH4HCO3, pH 7.8. The Kunitz-type inhibitor is eluted with 20 mM NH4HCO3, pH 7.8.

The Kunitz-type inhibitor is further purified and concentrated by chromatography on a Mono S column (Pharmacia-LKB Biotechnology AS, Alleroed, Denmark; 0.5×5 cm) equilibrated with 20 mM Bicine, pH 8.7. After washing with the equilibration buffer at 2 ml/min for 10 minutes, gradient elution of the Kunitz-type inhibitor is carried out over twelve minutes at 1 ml/min from 0–0.6M NaCl in the equilibration buffer. Peak samples are pooled, and the Kunitz-type inhibitor is purified using reverse phase HPLC on a Vydac 214TP510 column (Mikro-lab, Aarhus, Denmark; 1.0×25 cm) with a gradient elution at 4 ml/min from 5% A (0.1% trifluoroacetic acid (TFA) in water) to 45% B (0.7% TFA in acetonitrile) in 20 minutes. The purified product in lyophilized in water, and inhibitor activity is measured.

Kunitz inhibitor activity is measured using the method essentially described by Norris et al. (ibid.). Briefly, various fixed concentrations of the Kunitz-type inhibitor are incubated in the presence of 0.24 μg/ml of porcine trypsin (Novo Nordisk A/S, Bagsvaerd, Denmark), 12.8 CU/l human plasmin (Kabi, Stockholm, Sweden) or 0.16 nkat/ml human plasma kallikrein (Kabi) in 100 mM NaCl, 50 mM Tris HCl, pH 7.4. After a 30 minute incubation the residual enzymatic activity is measured by the degradation of a solution containing 0.6 mM of either of the chromogenic peptidyl nitroanilide trypsin/plasmin substrates S2251 (D-Val-Leu-Lys-Nan; Kabi) or S2302 (D-Pro-Phe-Arg-Nan; Kabi) in assay buffer. The samples are incubated for 30 minutes after which the absorbance of each sample is measured at 405 nm. Plasmin or trypsin activity is measured as a decrease in absorbance at 405 nm. From the results, the apparent inhibition constant Ki is calculated.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated DNA molecule encoding a human Kunitz-type inhibitor wherein said Kunitz-type inhibitor comprises the amino acid sequence of Sequence ID No. 2 from alanine, amino acid 56 to alanine, amino acid number 110; the amino acid sequence of Sequence ID No. 2 from aspartic acid, amino acid number 53 to alanine, amino acid number 110; or the amino acid sequence of Sequence ID No. 2 from valine, amino acid number 57 to alanine, amino acid number 110 and which further contains a glutamic acid residue on the amino terminus.

2. An isolated DNA molecule according to claim 1, wherein said DNA segment comprises the sequence of nucleotides of Sequence ID No. 1 from nucleotide 171 to nucleotide 331 or the sequence of nucleotides of Sequence ID No. 1 from nucleotide 159 to nucleotide 331.

3. A DNA construct comprising a first DNA segment encoding a human Kunitz-type inhibitor, wherein said Kunitz-type inhibitor comprises the amino acid sequence of Sequence ID No. 2 from alanine, amino acid 56 to alanine, amino acid number 110; the amino acid sequence of Sequence ID No. 2 from aspartic acid, amino acid number 53 to alanine, amino acid number 110; or the amino acid sequence of Sequence ID No. 2 from valine, amino acid number 57 to alanine, amino acid number 110 and which further contains a glutamic acid residue on the amino terminus, wherein said first DNA segment is operably linked to additional DNA segments required for the expression of said first DNA segment.

4. A DNA construct according to claim 3 wherein said first DNA segment comprises the sequence of nucleotides of Sequence ID No. 1 from nucleotide 171 to nucleotide 331 or the sequence of nucleotides of Sequence ID No. 1 from nucleotide 159 to nucleotide 331.

5. A host cell containing a DNA construct comprising a first DNA segment encoding a human Kunitz-type inhibitor, wherein said Kunitz-type inhibitor comprises the amino acid sequence of Sequence ID No. 2 from alanine, amino acid 56 to alanine, amino acid number 110; the amino acid sequence of Sequence ID No. 2 from aspartic acid, amino acid number 53 to alanine, amino acid number 110; or the amino acid sequence of Sequence ID No. 2 from valine, amino acid number 57 to alanine, amino acid number 110 and which further contains a glutamic acid residue on the amino terminus, wherein said first DNA segment is operably linked to additional DNA segments required for the expression of said first DNA segment.

6. A host cell according to claim 5, wherein said first DNA segment consists of the sequence of nucleotides of Sequence ID No. 1 from nucleotide 171 to nucleotide 331 or the sequence of nucleotides of Sequence ID No. 1 from nucleotide 159 to nucleotide 331.

7. An isolated DNA molecule encoding a human amyloid protein precursor homolog, wherein said amyloid protein precursor homolog comprises the amino acid sequence of Sequence ID No. 2 from alanine, amino acid number 1, to asparagine, amino acid number 132.

8. An isolated DNA molecule according to claim 7 wherein said DNA segment consists of the sequence of nucleotides of Sequence ID No. 1 from nucleotide 1 to nucleotide 399.

9. A DNA construct comprising a first DNA segment up to 3.5 kb in length encoding a human amyloid protein precursor homolog, wherein said amyloid protein precursor homolog comprises the amino acid sequence of Sequence ID No. 2 from alanine, amino acid number 1, to Asparagine, amino acid number 132, wherein said first DNA segment is operably linked to additional DNA segments required for the expression of said first DNA segment.

10. A DNA construct according to claim 9 wherein said first DNA segment consists of the sequence of nucleotides of Sequence ID No. 1 from nucleotide 1 to nucleotide 399.

11. A host cell containing a DNA construct comprising a first DNA segment up to 3.5 kb in length encoding a human amyloid protein precursor homolog, wherein said amyloid protein precursor homolog comprises the amino acid sequence of Sequence ID No. 2 from alanine, amino acid number 1, to Asparagine, amino acid number 132, wherein said first DNA segment is operably linked to additional DNA segments required for the expression of said first DNA segment.

12. A host cell according to claim 11 wherein said first DNA segment consists of the sequence of nucleotides of Sequence ID No. 1 from nucleotide 1 to nucleotide 399.

13. An *E. coli* host cell containing plasmid ZGKI20 (ATCC 69089) or plasmid ZGKI13 (ATCC 69090).

* * * * *